(12) United States Patent
Hattori

(10) Patent No.: US 7,879,215 B2
(45) Date of Patent: Feb. 1, 2011

(54) ELECTROPHORESIS CHIP

(75) Inventor: Wataru Hattori, Tokyo (JP)

(73) Assignee: NEC Corporation, Tokyo (JP)

( * ) Notice: Subject to any disclaimer, the term of this patent is extended or adjusted under 35 U.S.C. 154(b) by 225 days.

(21) Appl. No.: 12/344,009

(22) Filed: Dec. 24, 2008

(65) Prior Publication Data

US 2009/0166206 A1     Jul. 2, 2009

(30) Foreign Application Priority Data

Dec. 28, 2007   (JP)   ............... 2007-340363

(51) Int. Cl.
*G01N 27/453*   (2006.01)
(52) U.S. Cl. ...................... 204/603; 204/601
(58) Field of Classification Search ......... 204/601–605, 204/451–455
See application file for complete search history.

(56) References Cited

U.S. PATENT DOCUMENTS

| 7,586,091 | B2 * | 9/2009 | Takahashi et al. | ........... 250/288 |
| 2002/0023840 | A1 * | 2/2002 | Johnson et al. | ............. 204/454 |
| 2008/0023331 | A1 * | 1/2008 | Hattori | ....................... 204/451 |

FOREIGN PATENT DOCUMENTS

| JP | 2006266795 A | 10/2006 |
| WO | 03/071263 A1 | 12/2002 |
| WO | 2005124332 A1 | 12/2005 |

OTHER PUBLICATIONS

Ken Tseng et al., "Fabrication and Design of Open Microchannels for Capillary Electrophoresis Separations and Matrix-assisted Laser/Desorption Mass Spectrometry Analysis", SPIE Conference on Micro-and Nanofabricated Structures and Devices for Biomedical Environmental Application II, San Jose, California, (Jan. 1999), SPIE vol. 3606, pp. 137-148.

Jun Liu et al., "Electrophoresis Separation in Open Microchannels. A Method for Coupling Electrophoresis and MALDI=MS", Analytical Chemistry, vol. 73, No. 9, (May 1, 2001), pp. 2147-2151.

Michelle L.-S Mok et al., "Capillary Isoelectric Focusing in Pseudo-closed Channel Coupled to Matrix Assisted Laser Desorption/Ionization Mass Spectrometry for Protein Analysis", The Analyst, 2004, vol. 129, pp. 109-111.

* cited by examiner

*Primary Examiner*—Alex Noguerola

(57) ABSTRACT

An electrophoresis chip is provided with a channel that is filled with a solution in which a sample is dissolved, the electrophoresis chip being configured to carry out electrophoresis by applying voltage along the channel in a state in which the channel is hermetically sealed to separate the sample in the channel, and after this electrophoresis is performed, to carry out mass spectrometry by scanning a laser along the channel in a state in which the channel is open to an environment in which gas is present. A pattern is formed on the bottom surface of the channel to hold the solution as droplets. This pattern is made into a pattern in which hydrophilic areas are surrounded by hydrophobic areas and sidewalls of the channel.

10 Claims, 13 Drawing Sheets

(A-A')

(B-B')

(A-A')

(B-B')

ELECTROPHORESIS CHIP

INCORPORATION BY REFERENCE

This application is based upon and claims the benefit of priority from Japanese Patent Application No. 2007-340363, filed on Dec. 28, 2007, the disclosure of which is incorporated herein in its entirety by reference.

BACKGROUND OF THE INVENTION

1. Field of the Invention

The present invention relates to an electrophoresis chip that is used for separating a sample such as proteins in a channel by electrophoresis and then carrying out a process to detect the sample.

2. Description of the Related Art

The following system was recently proposed. In this system, a microfluidic chip that adopts a configuration in which a lid that covers the upper surface of a channel can be detached is used to first separate a solute of, for example, proteins contained in a sample solution in the channel by capillary-electrophoresis in a state in which the lid hermetically seals the channel. An ionization accelerator referred to as a matrix for assisting the ionization of the solute of protein is next added in a state in which the lid is detached and a matrix-assisted laser desorption/ionization mass spectrometer (MALDI-MS) is next used to ionize the solute by scanning with a laser along the channel on a microfluidic chip and then to detect the solute by mass spectrometry.

Systems for detecting by mass spectrometry are also proposed in the papers by K. Tseng et. al in SPIE (Vol. 3606 (1999) pp. 137-148), J. Liu et. al in Analytical Chemistry (Vol. 73 (2001), pp. 2147-2151), and M. Mok et. al in Analyst (Vol. 129 (2004), pp. 109-111), as well as in the documents JP-A-2003-071263 and JP-A-2005-124332. In these documents, systems are proposed that use a construction having an open upper surface formed on the surface of a microfluidic chip, i.e., a groove-shaped channel that lacks a lid structure for covering the channel, to separate a solute of, for example, proteins included in a sample solution in the channel using capillary-electrophoresis, and then use a matrix-assisted laser desorption/ionization mass spectrometer to ionize the solute by scanning the solute with a laser along the channel on the microfluidic chip and detect it by mass spectrometry. In these systems, the solute that has been separated in the channel is dried so as not to disrupt the separated state, a solution in which an ionization accelerator referred to as a "matrix" has been dissolved is added to the separated and dried solute to produce a matrix crystal in a state in which the sample is mixed, following which mass spectrometry is carried out.

In the systems described above, however, when the detected proteins are identified by using peptide mass fingerprinting (PMF), a process is necessary for adding a solution that contains a digestive enzyme such as trypsin to the protein while taking care not to disturb the positions of the proteins that have been separated in the channel to digest and break down in the peptides. The original proteins can be identified by subjecting these peptides to mass spectrometry. In this digestion process, in contrast to operations that are completed instantaneously such as when adding the matrix solution, the solution state must be maintained for at least several minutes. As a result, keeping the position of the proteins undisturbed in the digestion process is problematic in the case of the ordinary channel construction described in the documents mentioned hereinabove. In other words, a special channel is required that functions in specific cases as a flow path for electrophoresis to achieve a state in which the liquid is continuously contiguous in the channel while in other specific cases the special channel functions as wells in which droplets to not mix.

As such a channel, a construction can be considered in which theoretically, as shown in FIG. 1, channel 102 of a two-step excavated construction is formed that creates steps in the direction of depth of chip substrate 101. Such a construction can function as a flow path when there is a large volume of solution, but when there is a small volume of solution, portions 103 that are one level deeper can function as wells to prevent mixture of droplets of solution between the wells.

However, when a channel of this construction is actually produced, the amount of liquid that is handled on a microfluidic chip is extremely small, and the effect of gravity is therefore limited and the effect of hydrophilic or hydrophobic properties greater than that of gravity. Accordingly, maintaining solution independently in each well is problematic when only the depth of the channel is increased, and filling wells with solution is also problematic.

SUMMARY OF THE INVENTION

It is an object of the present invention to solve the above-described problems by providing an electrophoresis chip that can realize a channel that acts as a flow path under specific conditions and that acts as wells that can stably keep droplets independent in each well in the channel under specific conditions and that can further improve processing in an analysis system.

To achieve the above-described objects, the electrophoresis chip according to the present invention is provided with a channel that is filled with a solution in which a sample is dissolved and is configured to implement electrophoresis by applying voltage along the channel in a state in which the channel is hermetically sealed to separate the sample in the channel, and following electrophoresis, to carry out mass spectrometry of the sample by scanning a laser along the channel in a state in which the channel is open to an environment in which gas is present. A pattern for holding a solution as droplets is formed on the bottom surface of the channel, and this pattern is made into a pattern in which a first hydrophilic area is surrounded by at least a second hydrophilic area in which the hydrophilic property is lower than that of the first hydrophilic area.

In addition, another electrophoresis chip according to the present invention is provided with a channel that is filled with a solution in which a sample is dissolved and is configured to implement electrophoresis by applying voltage along the channel in a state in which the channel is hermetically sealed to separate the sample in the channel, and following electrophoresis, to carry out mass spectrometry of the sample by scanning a laser along the channel in a state in which the channel is open to an environment in which gas is present. A pattern for holding the solution as droplets is formed on the bottom surface of the channel, and this pattern is made into a pattern in which a hydrophilic area is surrounded by at least a hydrophobic area.

According to the present invention, a channel can be realized in which under specific conditions functions as a flow path and in which under specific conditions functions as wells that can stably hold droplets independently in the channel. Accordingly, the present invention can realize an improved process that previously could not be achieved, whereby proteins that have been separated by electrophoresis and that have been detected are identified by means of PMF.

DETAILED DESCRIPTION OF THE PREFERRED EMBODIMENTS

First Embodiment

Figure 1:
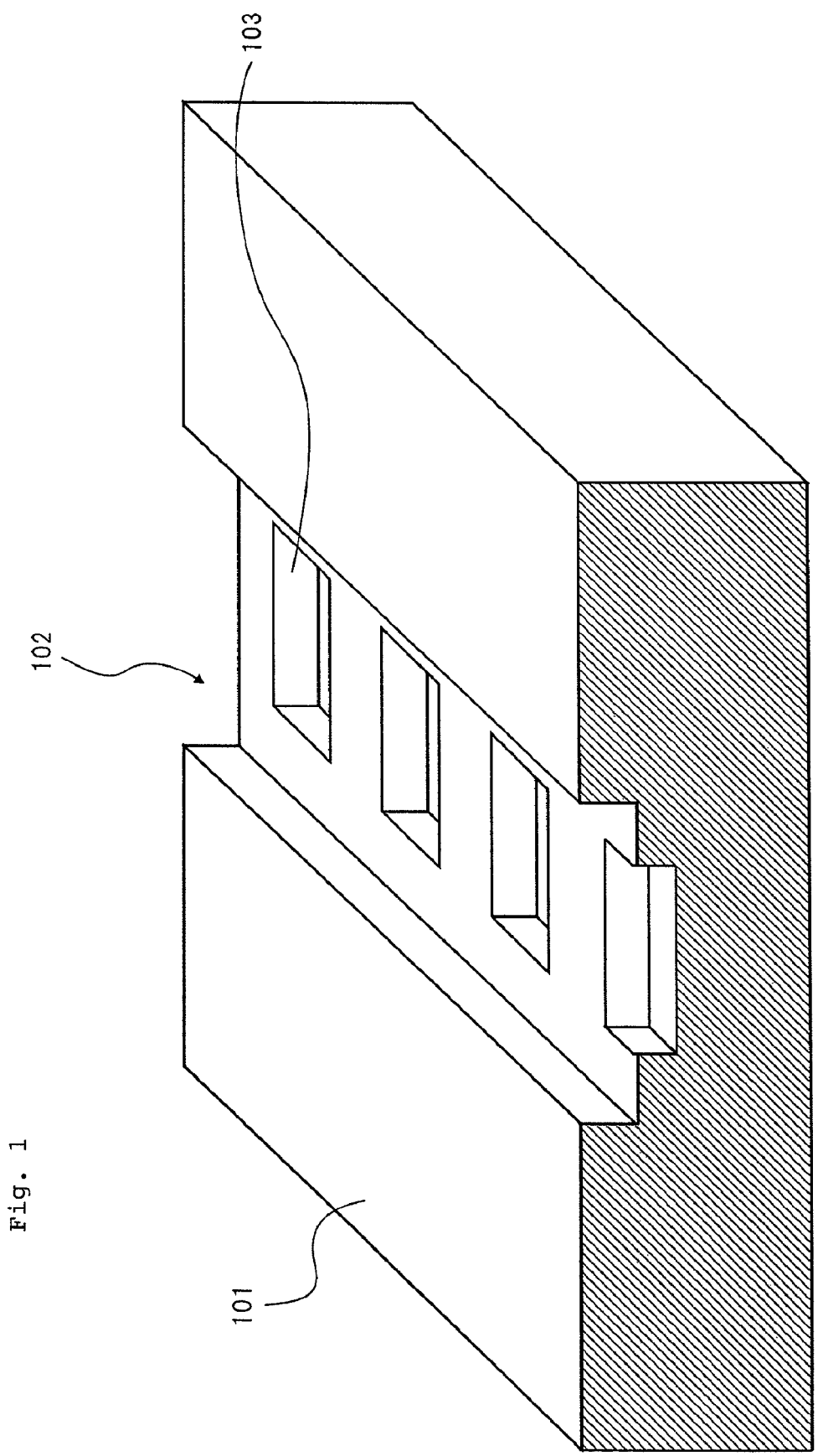
FIG. 1 is a schematic perspective view showing the configuration of an electrophoresis chip that has a channel that has a two-step configuration.
Figure 2A:
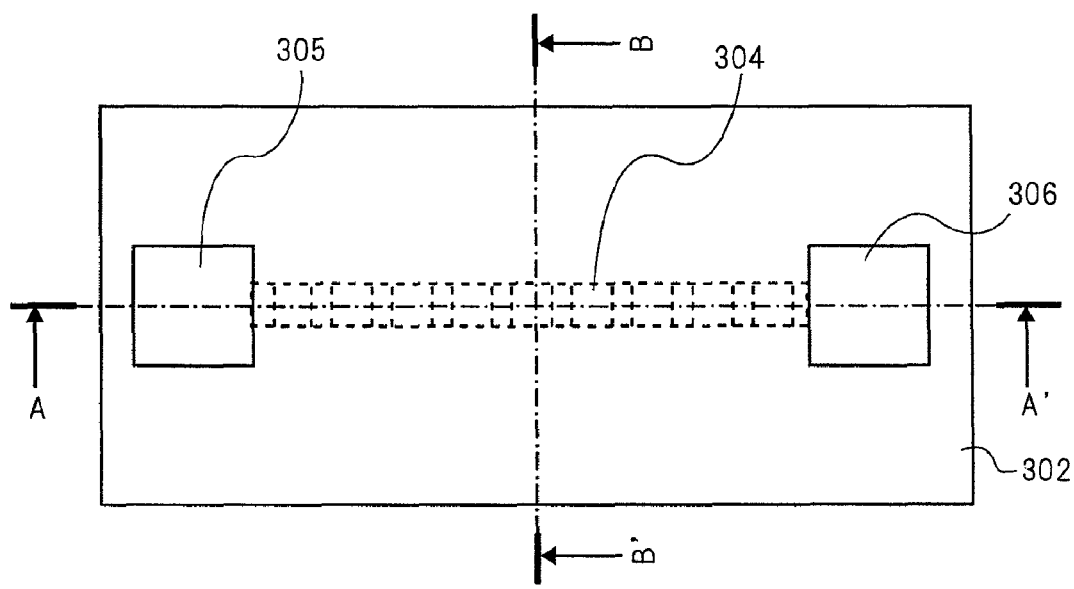
FIG. 2A is a plan view showing the electrophoresis chip of an embodiment in which a channel is hermetically sealed by a cover.
Figure 2B:
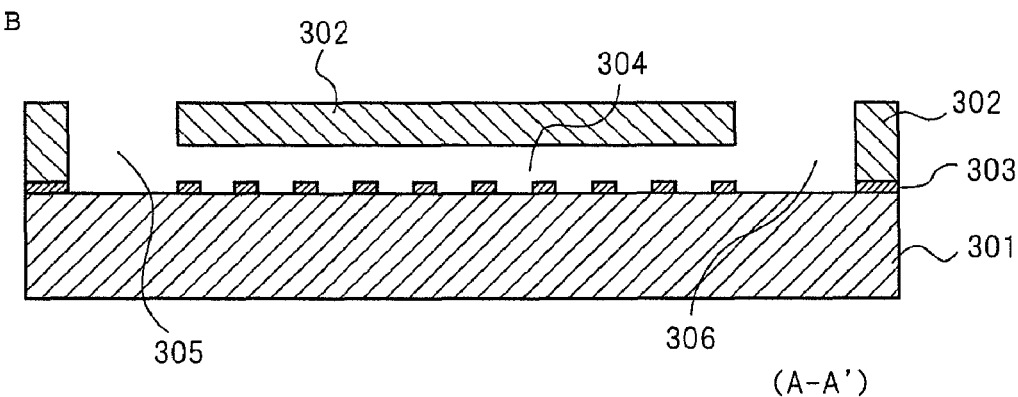
FIG. 2B is a sectional view taken along line A-A' that shows the electrophoresis chip of an embodiment in which a channel is hermetically sealed by a cover.
Figure 2C:
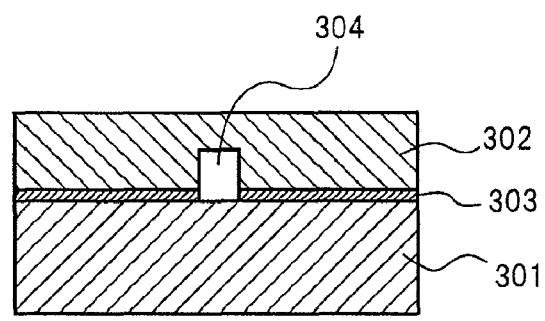
FIG. 2C is a sectional view taken along line B-B' that shows the electrophoresis chip of an embodiment in which a channel is hermetically sealed by a cover.

FIG. 2A is a plan view showing an electrophoresis chip of an embodiment in which a channel is hermetically sealed by a cover, FIG. 2B is a sectional view taken along line A-A' of FIG. 2A, and FIG. 2C is a sectional view taken along line B-B' of FIG. 2A.

As shown in FIGS. 2A-2C, the electrophoresis chip of the present embodiment is of a configuration in which the surface of chip substrate 301 is covered with cover 302. As the material of chip substrate 301 a hydrophilic material such as glass may be used or a water-repellant material such as a typical plastic may be used, but a hydrophilic material is used in the present embodiment. A pattern composed of water-repellant film 303 is formed on the surface of chip substrate 301 that is composed of a hydrophilic material. Water-repellant film 303 is formed by patterning a fluorocarbon resin film, a hydrophobic area being formed by this water-repellant film 303.

In the present embodiment, in particular, a portion that lacks water-repellant film 303 is formed on the upper surface portion of chip substrate 301 that corresponds to the bottom surface of channel 304. The material of chip substrate 301 is exposed on the surface of the portion that lacks water-repellant film 303 and therefore exhibits a hydrophilic property. In the case of an electrophoresis chip, a hydrophilic coating of polyethylene glycol or polyacrylamide may be provided on the surface in which the above-described material of chip substrate 301 is exposed to suppress electroendosmose flow. Cover 302 is preferably formed of an adsorptive material such as silicone rubber to enable detachment from chip substrate 301. In this way, electrophoresis can be implemented without leakage of liquid from channel 304.

As shown in FIG. 2C, channel 304 is formed by processing to a groove shape on the lower surface of cover 302 that faces the surface of chip substrate 301. If the electrophoresis chip of the present embodiment is assumed to be a chip that performs isoelectric focusing, channel 304 is formed to join reservoir 305 and reservoir 306 in a straight line. Channel 304 is filled with a sample solution containing ampholyte and in which proteins and peptides are mixed as the sample to be separated. In addition, reservoirs 305 and 306 are filled with acidic and alkaline liquids for use as electrodes and voltage is applied along channel 304 with the acidic side being the cathode and the alkaline side being the anode. A hydrogen ion concentration gradient is formed in channel 304 by the application of this voltage. The proteins and peptides that are spread in channel 304 then shift in the channel and within several minutes collect according to the channel length and applied voltage at positions at which the hydrogen ion concentration matches the isoelectric point that is characteristic of each of these proteins and peptides.

According to the electrophoresis chip shown in FIGS. 2A-2C, channel 304 can be filled with the sample liquid when carrying out this isoelectric focusing. However, reducing the amount of liquid enables the formation of individual isolated droplets in hydrophilic areas that are surrounded by the sidewalls of the channel at cover 302 that is composed of hydrophobic silicone rubber and water-repellant film 303 that has been patterned.

Figure 3:
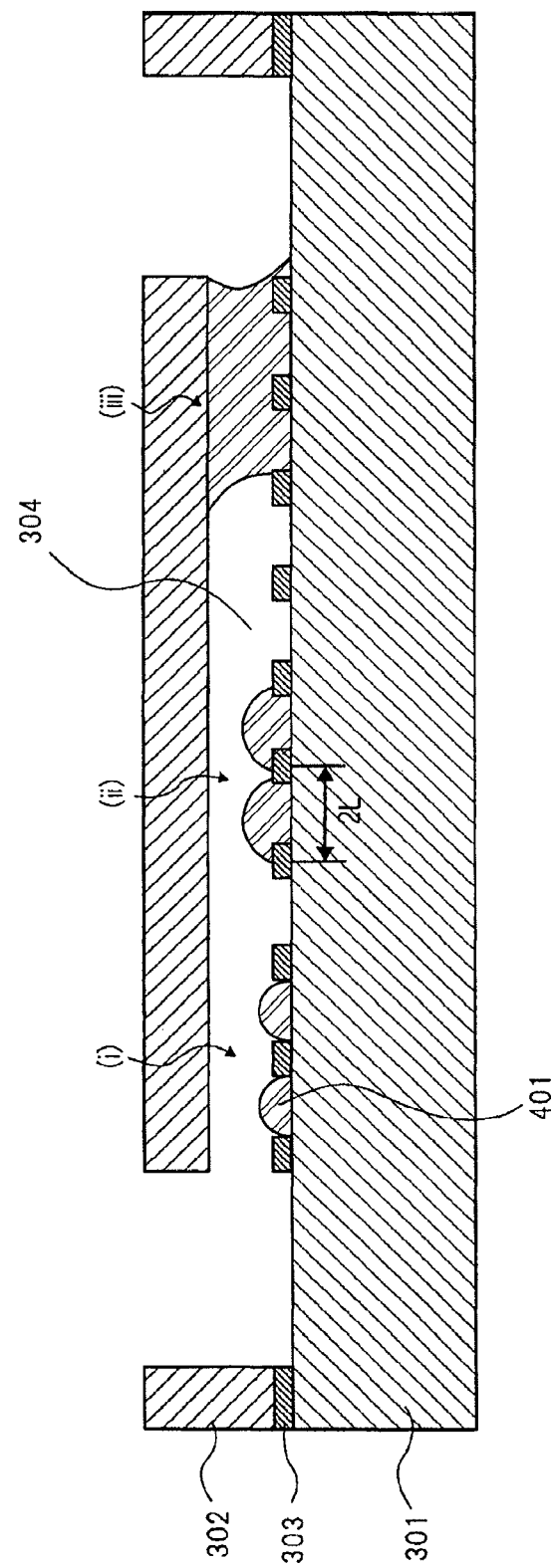
FIG. 3 is a view for explaining cases in which the amount of solution that is filed into the channel in FIG. 2B varies.

The following explanation regards the method of using the electrophoresis chip of the present embodiment with reference to FIG. 3. FIG. 3 shows cases in which the degree of filling of the channel in FIG. 2B with a solution is varied over three separate cases: (i), (ii), and (iii).

In case (i) in which the degree of filling of the channel with solution is sufficiently low, a droplet is formed in each hydrophilic area. Hydrophobic areas are present between these droplets, and because the droplets are drawn toward the hydrophilic areas that are surrounded by these hydrophobic areas, a force acts to divide the droplets in these areas. As a result, when the amount of solution is sufficiently small, the droplets are each divided by the hydrophobic areas and can exist as isolated droplets without being mixed between adjacent droplets. In other words, droplets are independently formed in hydrophilic areas without being mixed. Accordingly, the hydrophilic areas that are surrounded by the sidewalls of the channel at cover 302 that is made from hydrophobic silicone rubber and water-repellant film 303 that has been patterned act as wells that hold the solution as droplets.

In addition, the use of the effect of hydrophilic and hydrophobic properties that are stronger than gravity in the electrophoresis chip of the present embodiment allows droplets to be held stably. In addition, the operation of filling the wells with solution can be easily carried out due to the use of droplets that naturally form on the substantially flat surface of the chip substrate.

In case (ii) in which the degree of filling of the channel with solution is increased, droplets spread over the water-repellant film to form even larger droplets. In this case, the hydrophilic areas are in the vicinities of the centers of droplets whereby the positions of the droplets are fixed to these positions and thus more stabilized and stationary than a case in which the droplets are simply positioned on the water-repellant film. In the case of a configuration in which hydrophilic areas are not surrounded by the side-walls of the channel at cover 302 that is composed of a hydrophobic silicone rubber and a water-repellant film that has been patterned, droplets would not form independently, and the positions of the droplets would not be stable. In case (iii) in which amount of droplets that is filled into the channel is increased over case (ii), adjacent droplets contact each other to join as one, the droplets further contacting the lower surface of the cover and the solution filling channel 304. In this state, electrophoresis is possible in a state in which the solution completely fills the interior of channel 304.

According to the present embodiment as described hereinabove, a configuration is adopted in which differences between hydrophilic and hydrophobic properties are used to form a pattern on the bottom surface of a channel, and this pattern is formed such that hydrophilic areas are surrounded by hydrophobic areas and channel side-walls. By means of this configuration, a channel can be realized that acts as a flow path when the amount of liquid is great and that acts as wells that can each hold droplets in isolation in the channel when the amount of liquid is small. Accordingly, the electrophoresis chip of the present embodiment can realize improved processing that previously could not achieved in which, for example, the above-described proteins that have been separated and detected are identified by peptide mass fingerprinting (PMF).

Figure 4:
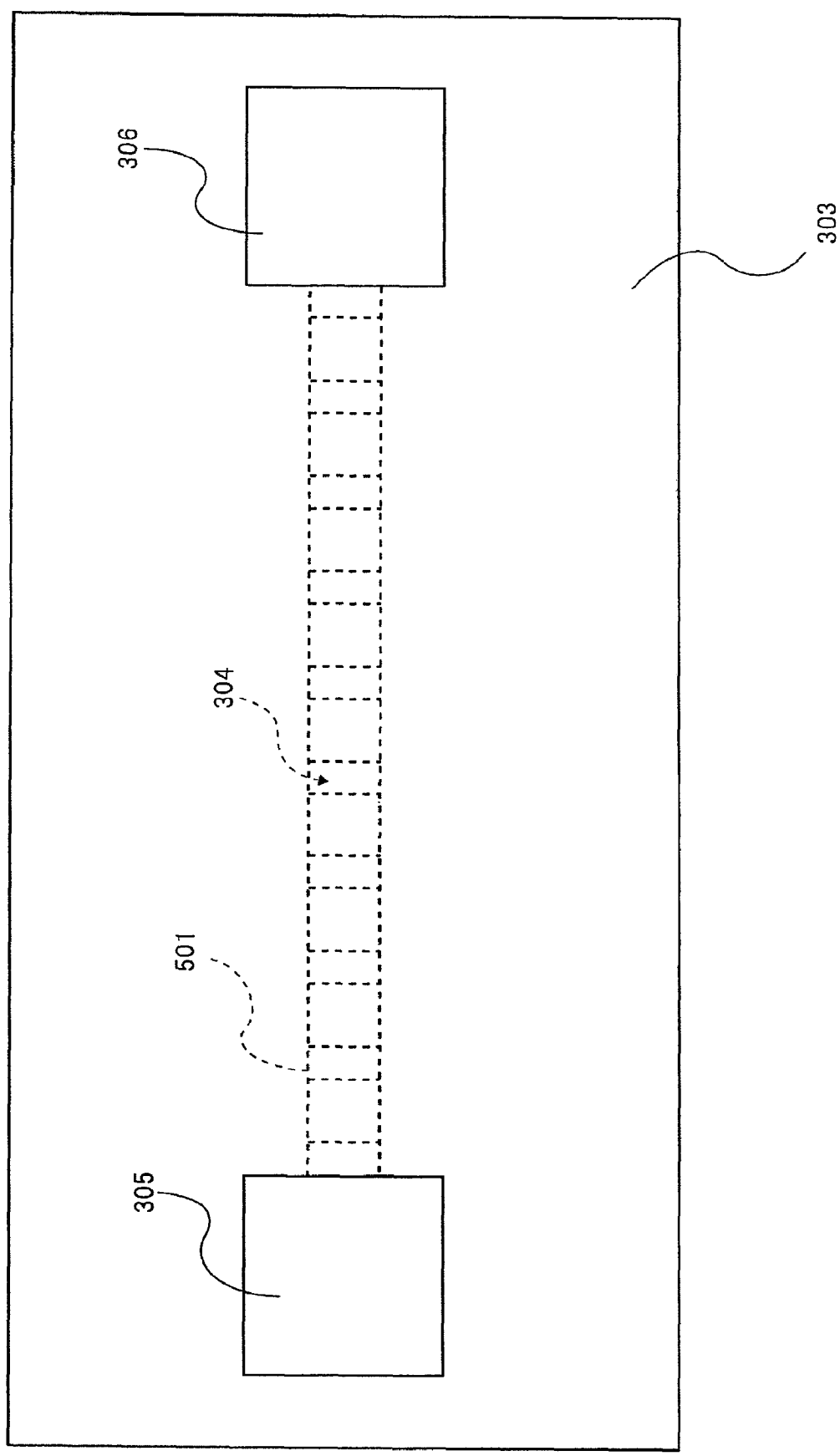
FIG. 4 is a plan view showing a pattern formed on the bottom surface of a channel by using differences of hydrophilic and hydrophobic properties.
Figure 5:
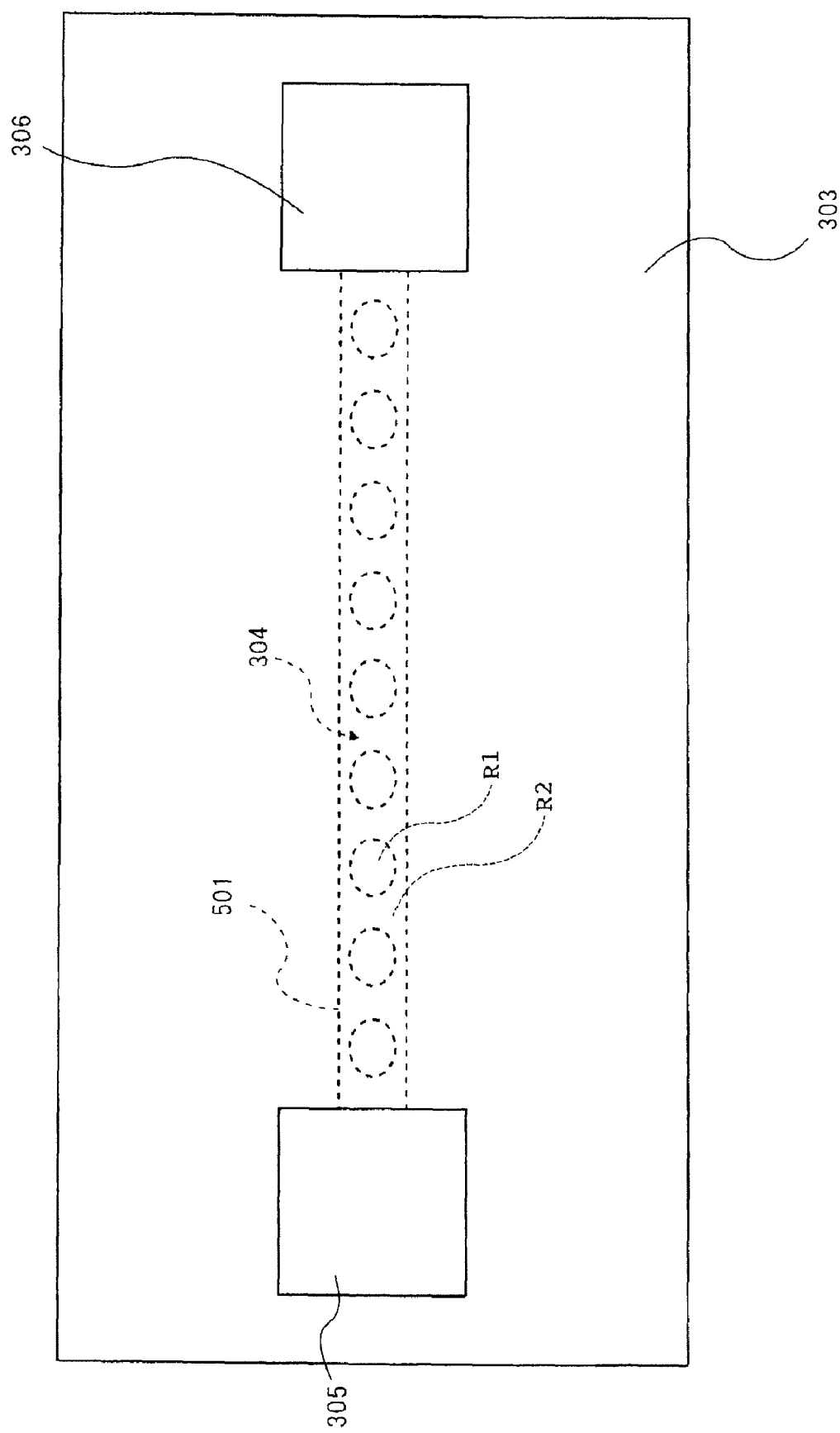
FIG. 5 is a plan view showing another example of the configuration in which differences of hydrophilic and hydrophobic properties are used to form a pattern on the bottom surface of a channel.

As the pattern of the bottom surface of the channel in the present embodiment, a pattern is used in which hydrophilic areas are enclosed by hydrophobic areas and side-walls 501 of channel 304 as shown in FIG. 4, but a pattern may also be used in which hydrophilic areas R1 are enclosed only by hydrophobic area R2 as shown in FIG. 5. When such a pattern is used, wells can be formed without regard to the hydrophilic property and hydrophobic property of the side-walls 501 of channel 304.

Figure 6:
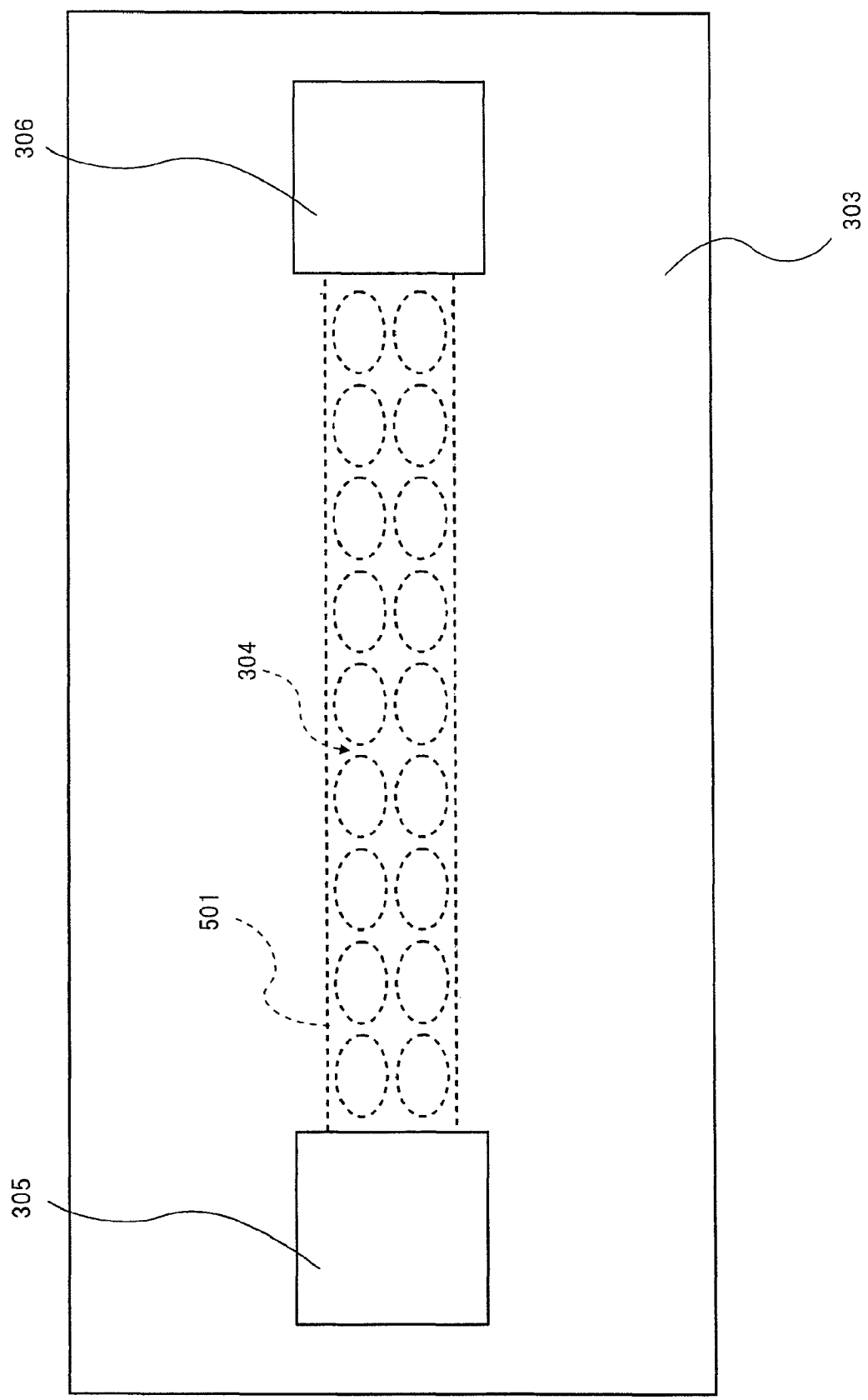
FIG. 6 is a plan view showing yet another example of the configuration in which differences of hydrophilic and hydrophobic properties are used to form a pattern on the bottom surface of a channel.

The pattern formed on the bottom surface of the channel is not limited to a configuration having a one well row realized by disposing a plurality of wells along the longitudinal direction of the channel and may be a pattern realized from two well rows as shown in, for example, FIG. 6. In the case of this configuration that has two well rows, the processes from detection to identification of proteins can be realized in a single separation by detecting parent ions of the proteins in a one well row and detecting the digests of these proteins in the other well row.

Figure 7:
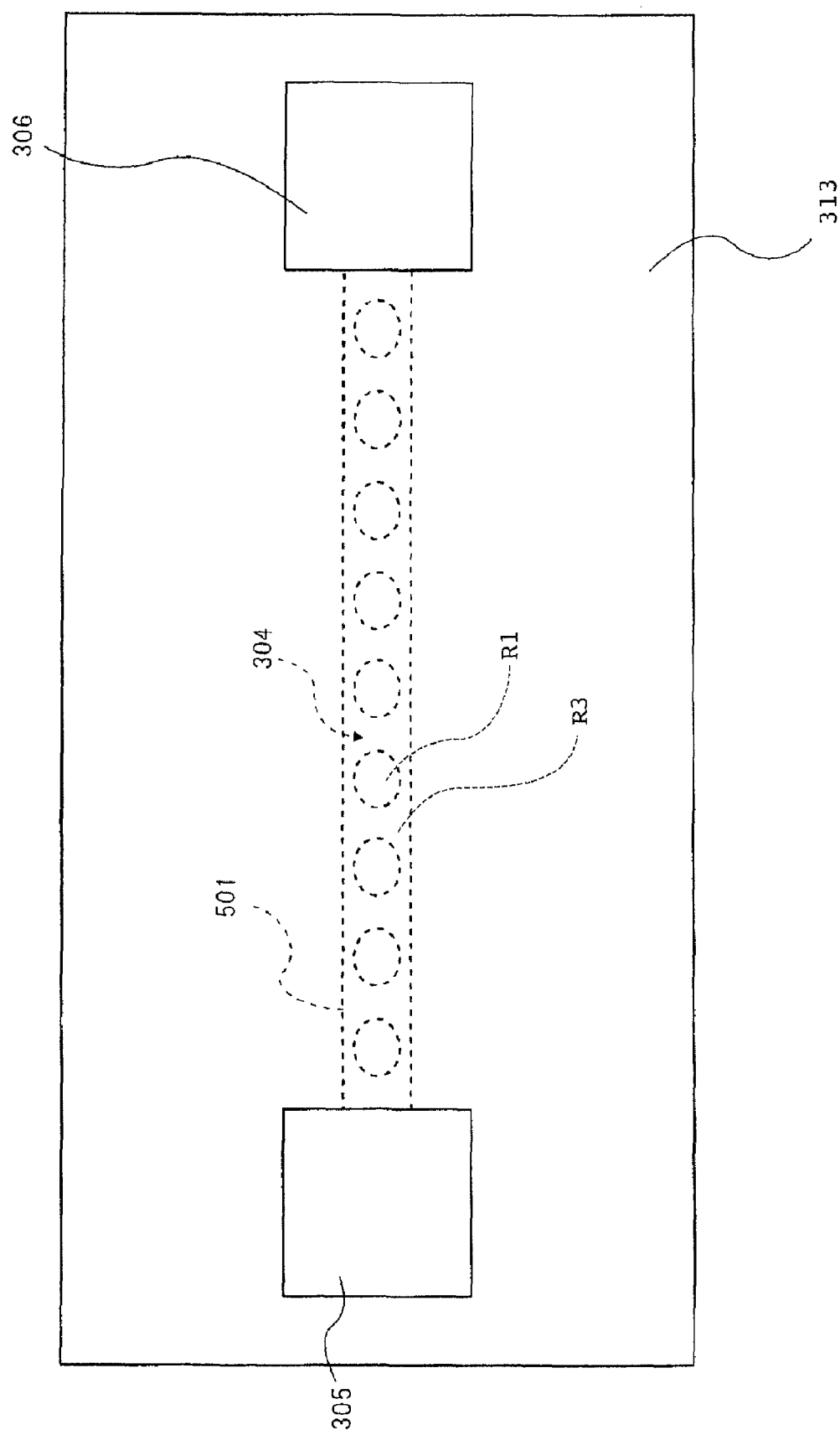
FIG. 7 is a plan view showing yet another example of the configuration in which differences of hydrophilic and hydrophobic properties are used to form a pattern on the bottom surface of a channel.

Further, although water-repellant film 303 that forms a hydrophobic area was used in the present embodiment, another thin film 313 may be used that is a film coating that makes up area R3 (second hydrophilic area) that has a lower hydrophilic property than area R1 (first hydrophilic area) that is formed by the surface of chip substrate 301 and that has a relatively high hydrophilic property, as shown in FIG. 7. In the case of this configuration, the angle of contact θ of droplets is low but the same effect as previously described can be obtained. In addition, the patterns shown in FIGS. 5 and 6 can also be similarly adopted in this configuration.

Still further, the hydrophilic property can be freely controlled by forming, on the bottom surface of the channel, an array construction made up by a plurality of protrusions that are sufficiently smaller than droplets, whereby the multiplication factor of the surface area of the bottom surface is changed by varying the density of this array construction. As the array construction made up from a plurality of protrusions that are sufficiently smaller than droplets, an array of micropillars approximately 50 microns or less, or a surface that has been roughened to a grained form that can be produced by sandblasting can be used.

This array construction allows an improvement in the degree of freedom for setting a pattern that is free of the limitations of inherent material constants that are attendant to the use of hydrophilic and hydrophobic properties that are characteristic of materials.

In particular, the use of micropillars formed through the use of a semiconductor microprocessing technology allows freedom in setting pillar formation and pillar arrangement and therefore enables freedom of the disposition of each area described hereinabove in the channel. In addition, according to the design of the pillar formation and pillar arrangement, directions that promote or impede flow of the solution can be freely set on the bottom surface of the channel to additionally enable a concentrating effect that progressively focuses droplets in prescribed positions with the drying of the solution.

Each individual pillar is preferably sufficiently smaller than the intended droplet size, pillars preferably being formed at no greater than one-tenth the droplet size. For example, forming a flow path that does not easily allow droplets on the order of 10-micron units requires the formation of column structures of the micron order. When these micropillars are formed to multiply, by a factor of two or more, the surface area of a chip substrate in which the angle of contact θ of the flat portion is less than 60°, the areas in which the pillars are formed exhibit an ultra-hydrophilic property as predicted based on the Wentzel equation, whereby a solution spreads limitlessly and without forming droplets. Accordingly, when the surface of this area is preferably inherently hydrophilic and the surface is hydrophilic, the effect of multiplying the surface area results in an extremely strong hydrophilic or ultra-hydrophilic property. In addition, setting the density of the pillar arrangement such that density varies enables the combination of effects such as the separation of the solution and the formation of droplets in a sparse area and the progressive concentration of the solution in a dense area.

Figure 8:
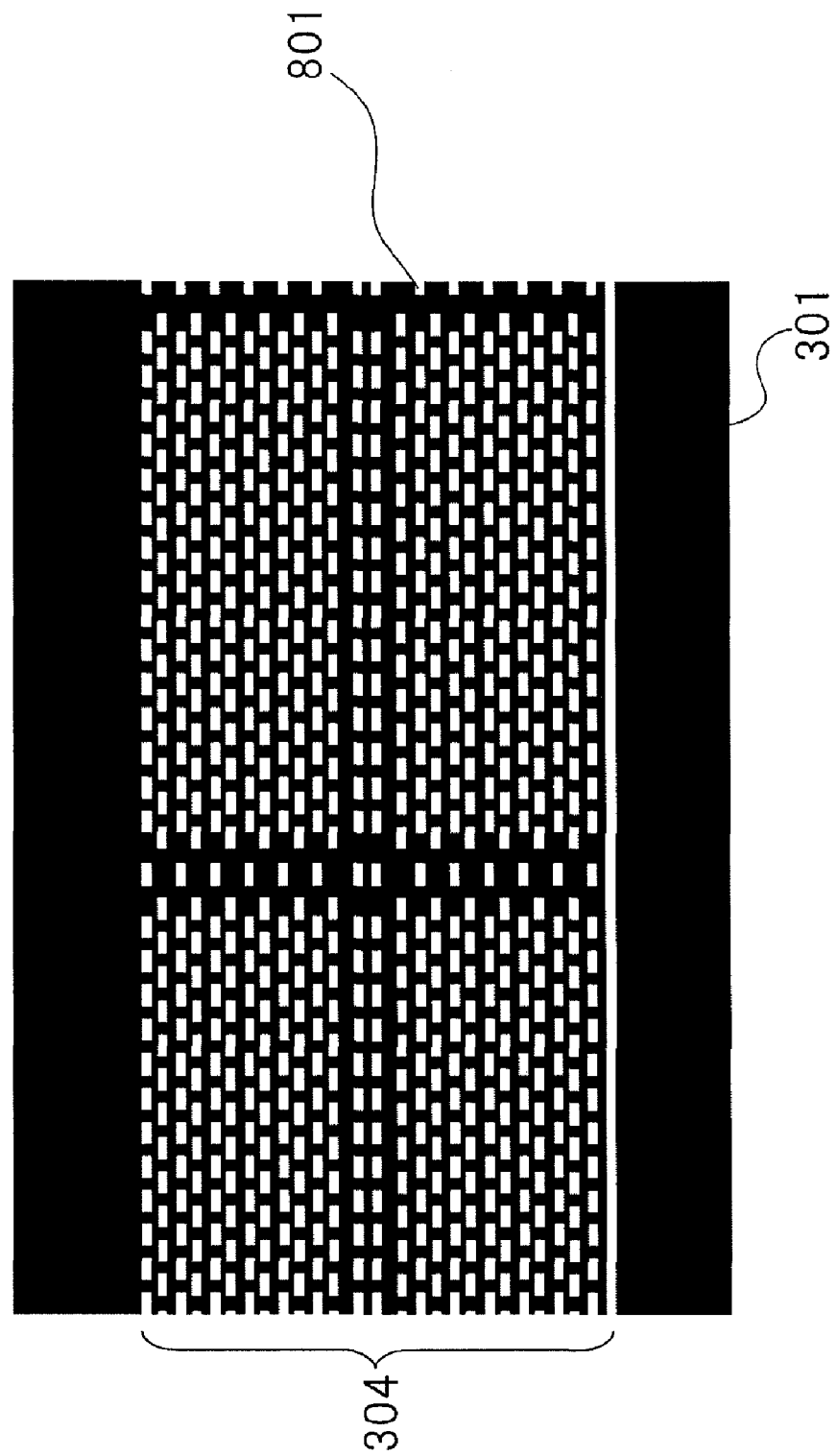
FIG. 8 shows an example of a pillar array in a channel.
Figure 9:
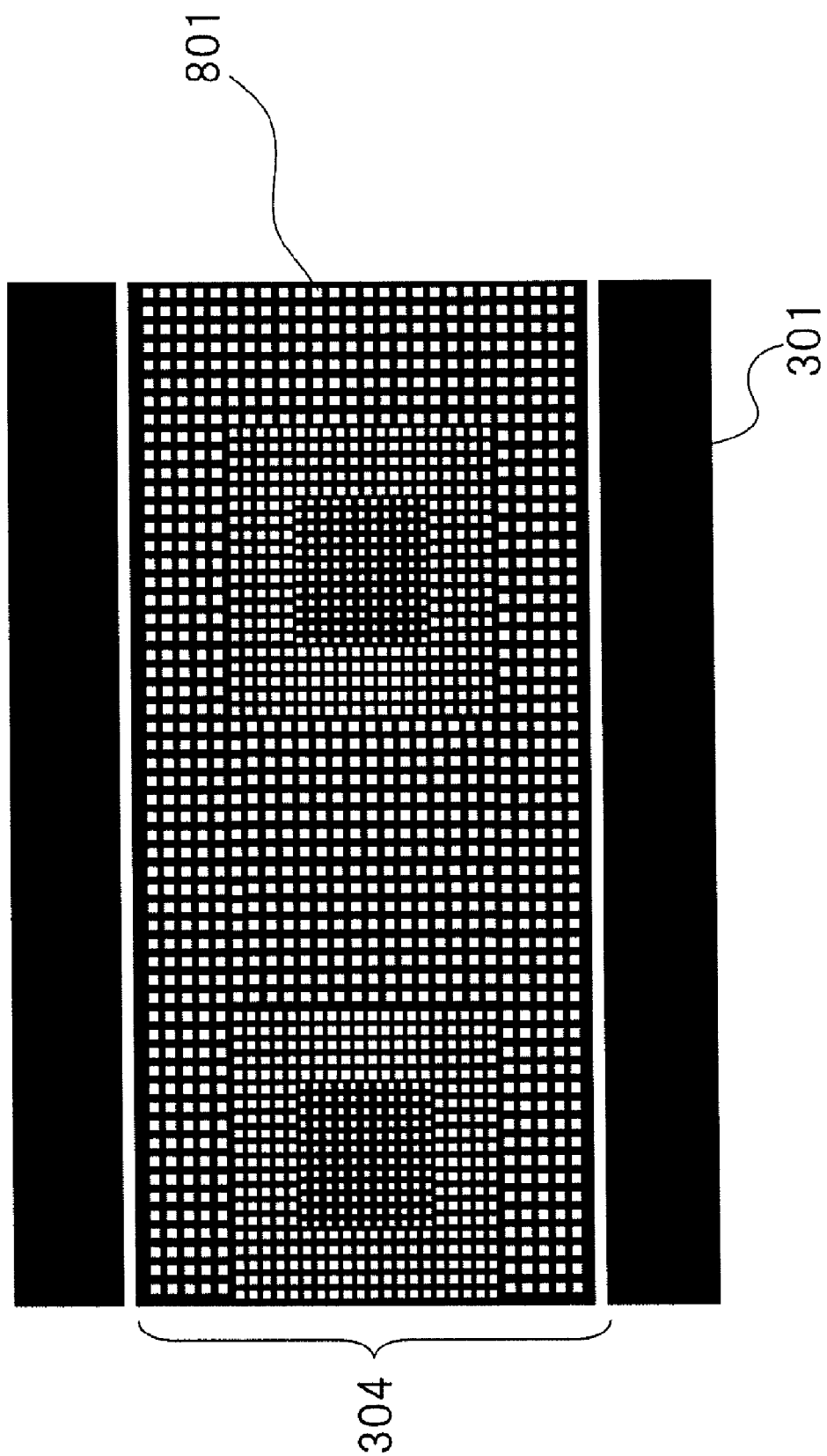
FIG. 9 shows another example of a pillar array.
Figure 10:
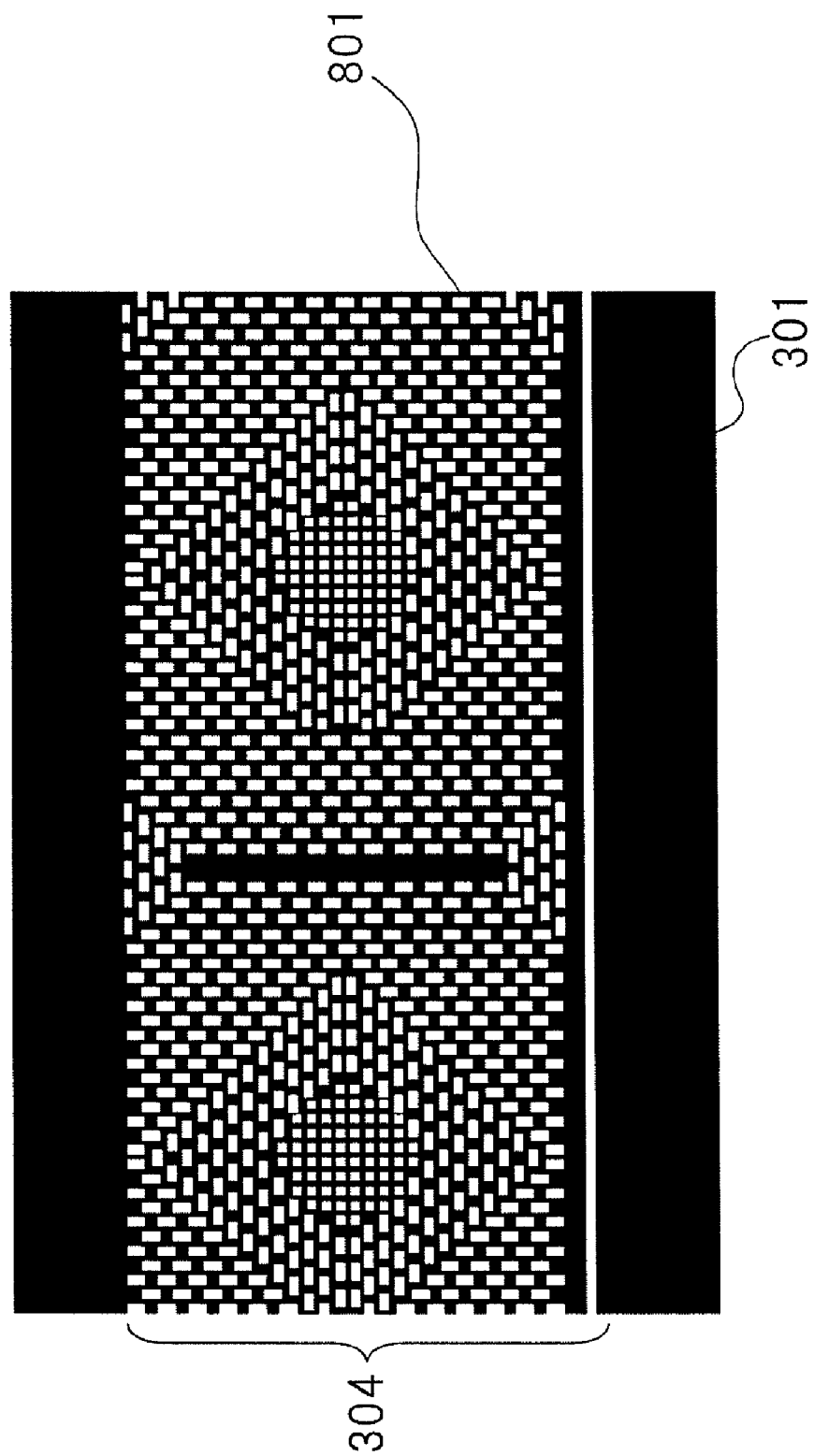
FIG. 10 shows yet another example of a pillar array.

As examples of pillar arrangements, scanning electron microscope images taken from the upper surfaces of electrophoresis chips of the pillar arrangements formed on the bottom surface of the channels are shown in FIGS. 8 to 10. In the example of a configuration shown in FIG. 8, each of the white points appearing in channel 304 indicates the uppermost surface of pillar 801, and differences in density, i.e., sparseness and denseness, have been formed in the pillar arrangement. In the portion in which the pillar arrangement is sparse, droplets are separated and divided. On the other hand, in the case of the configuration shown in FIG. 9, dense portions are formed in the pillar arrangement. When the solution is dried, droplets collect in these dense portions and dry, whereby the solute becomes concentrated in these dense portions.

The example of a configuration shown in FIG. 10 offers the effects of both the configuration shown in FIG. 8 and the configuration shown in FIG. 9. In this configuration, when liquid is dried and droplets are formed, the droplets are separated and divided by portions in which the pillar arrangement is sparse. On the other hand, separated droplets collect in the dense portions and are dried, whereby solute is precipitated in the dense portions. In other words, the portions in which the pillar arrangement is sparse correspond to areas having a low hydrophilic property (second hydrophilic areas), and portions in which the pillar arrangement is dense correspond to areas having a high hydrophilic property (first hydrophilic areas).

In the present embodiment, a pattern is formed on the bottom surface of the channel in which areas in which the hydrophilic property is relatively high are surrounded by areas in which the hydrophilic property is relatively low. A channel can thus be realized that functions as a flow path when the amount of liquid is great and that functions as wells that can each stably hold droplets in isolation in the channel when the amount of liquid is small.

Second Embodiment

Figure 11A:
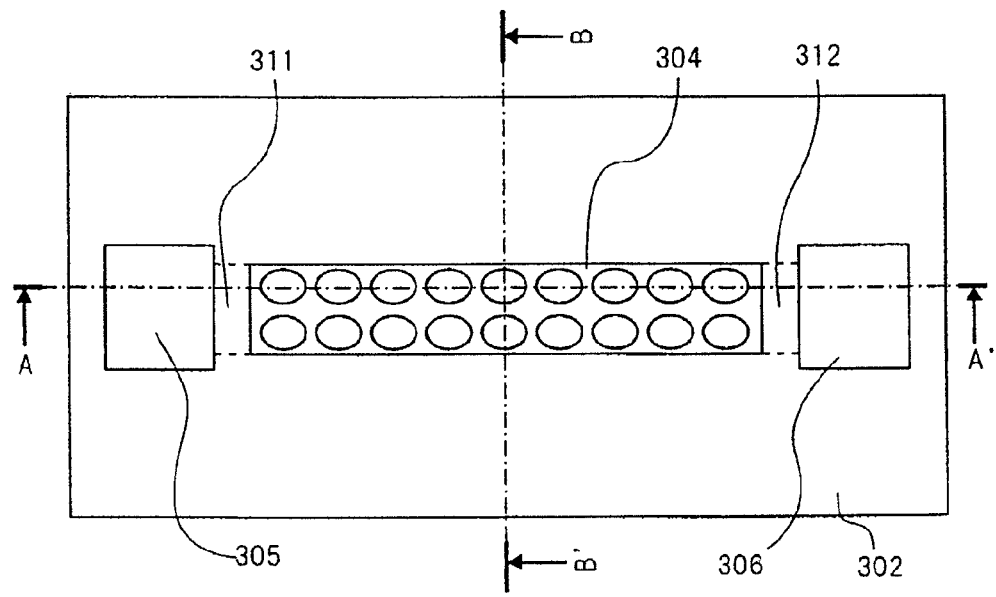
FIG. 11A is a plan view showing an electrophoresis chip of an embodiment that has a groove-shaped channel in which the solution in the channel is open to an environment in which gas is present.
Figure 11B:
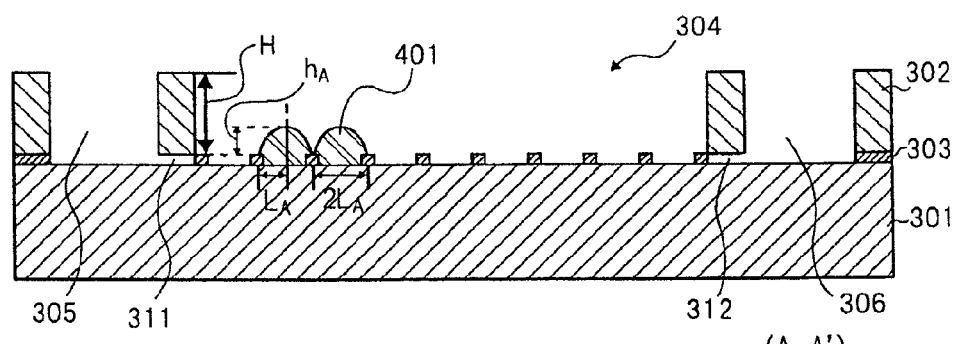
FIG. 11B is a sectional view taken along line A-A' showing an electrophoresis chip of an embodiment that has a groove-shaped channel in which solution in the channel is open to an environment in which gas is present.
Figure 11C:
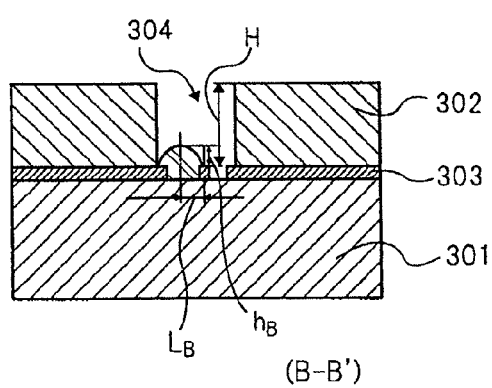
FIG. 11C is a sectional view taken along line B-B' showing an electrophoresis chip of an embodiment that has a groove-shaped channel in which solution in the channel is open to an environment in which gas is present.

FIG. 11A is a plan view showing an electrophoresis chip provided with a channel in a groove shape that adopts an open structure in which the upper surface of a solution in the channel comes into contact with gas. FIG. 11B is a sectional view taken along line A-A' of FIG. 11A, and FIG. 11C is a sectional view taken along line B-B' of FIG. 11A.

As in the first embodiment, the electrophoresis chip of the present embodiment is of a configuration in which cover 302 covers chip substrate 301. The material of chip substrate 301 may be a hydrophilic material such as glass or a water repellant material such as a typical plastic, but the present embodiment employs a hydrophilic material. A pattern composed of water-repellant film 303 is formed on chip substrate 301 that is composed of a hydrophilic material. Water-repellant film 303 that makes up the hydrophobic areas is obtained by patterning, for example, a fluorocarbon resin film.

In particular, in the present embodiment, a portion in which water-repellant film 303 is absent is formed on the upper surface portion of chip substrate 301 that corresponds to the bottom surface of channel 304. The material of chip substrate 301 is exposed on the surface of the portion that lacks water-repellant film 303 and this portion therefore exhibits a hydrophilic property. Further, in the case of an electrophoresis chip, a hydrophilic coating of polyethylene glycol or polyacrylamide may be provided to suppress electroendosmose flow on the above-described surface in which the material of chip substrate 301 is exposed. Alternatively, a configuration may be adopted in which a substrate made of a fluorocarbon resin or an acryl plastic is used as the chip substrate and a polyacrylamide coating then applied to this substrate and patterned.

Cover 302 is preferably formed using a material such as silicone rubber that is adsorptive to chip substrate 301 to enable detachment from chip substrate 301. By means of cover 302, electrophoresis can be carried out without leakage from channel 304. Channel 304 is formed by, for example, cutting cover 302 in the direction of thickness to a groove form. In other words, cover 302 functions as a frame member that forms the side-walls of channel 304. When the electrophoresis chip of the present embodiment is a chip for carrying out isoelectric focusing, channel 304 is formed to join reservoir 305 and reservoir 306 in a straight line. However, when mixing of the liquid in each of reservoirs 305 and 306 and the liquid in channel 304 is to be prevented, salt bridges or bottlenecks 311 and 312 may be provided as necessary between channel 304 and reservoirs 305 and 306 as shown in the figure.

Figure 12:
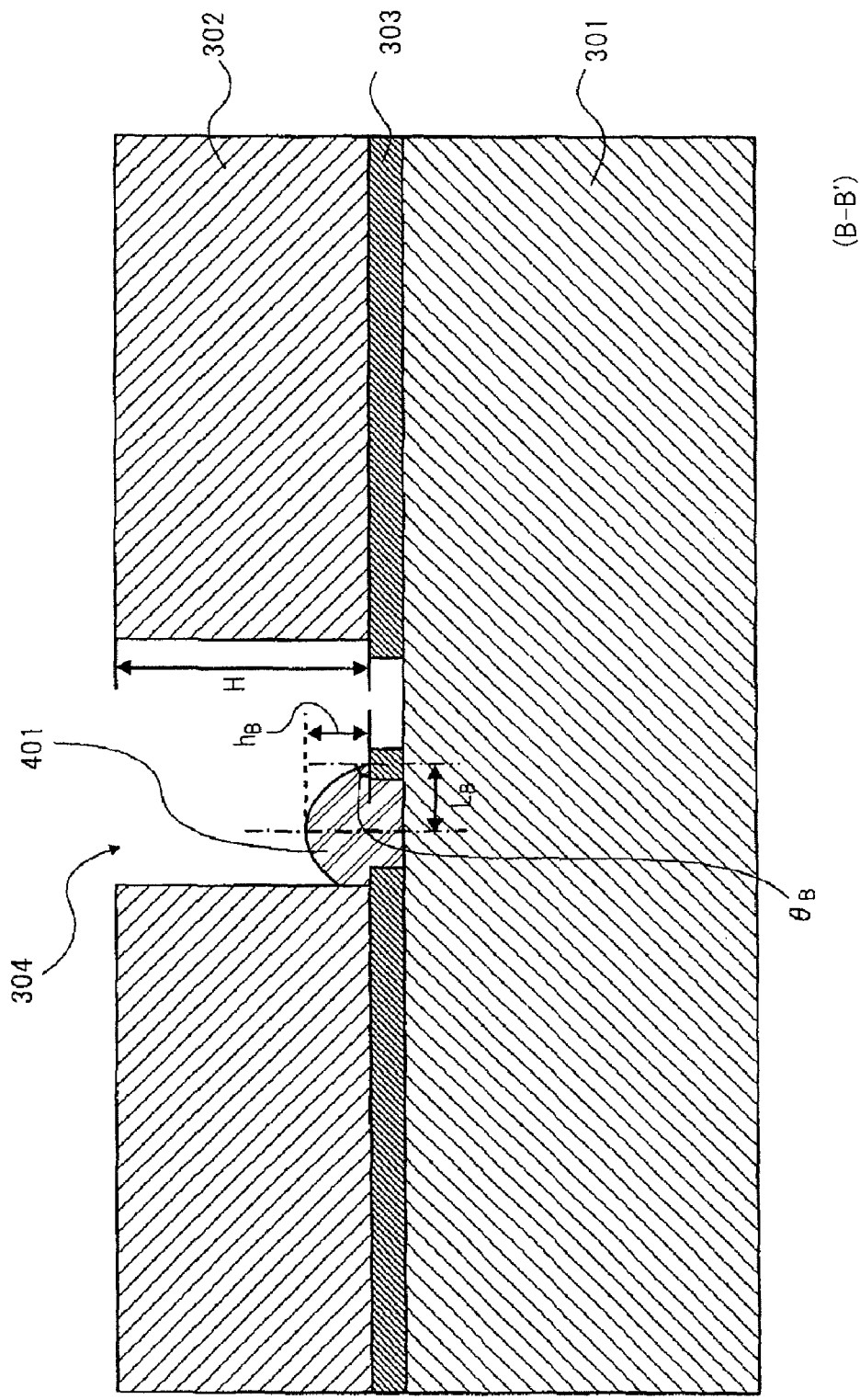
FIG. 12 is a sectional view showing an enlargement of FIG. 11C.
Figure 13:
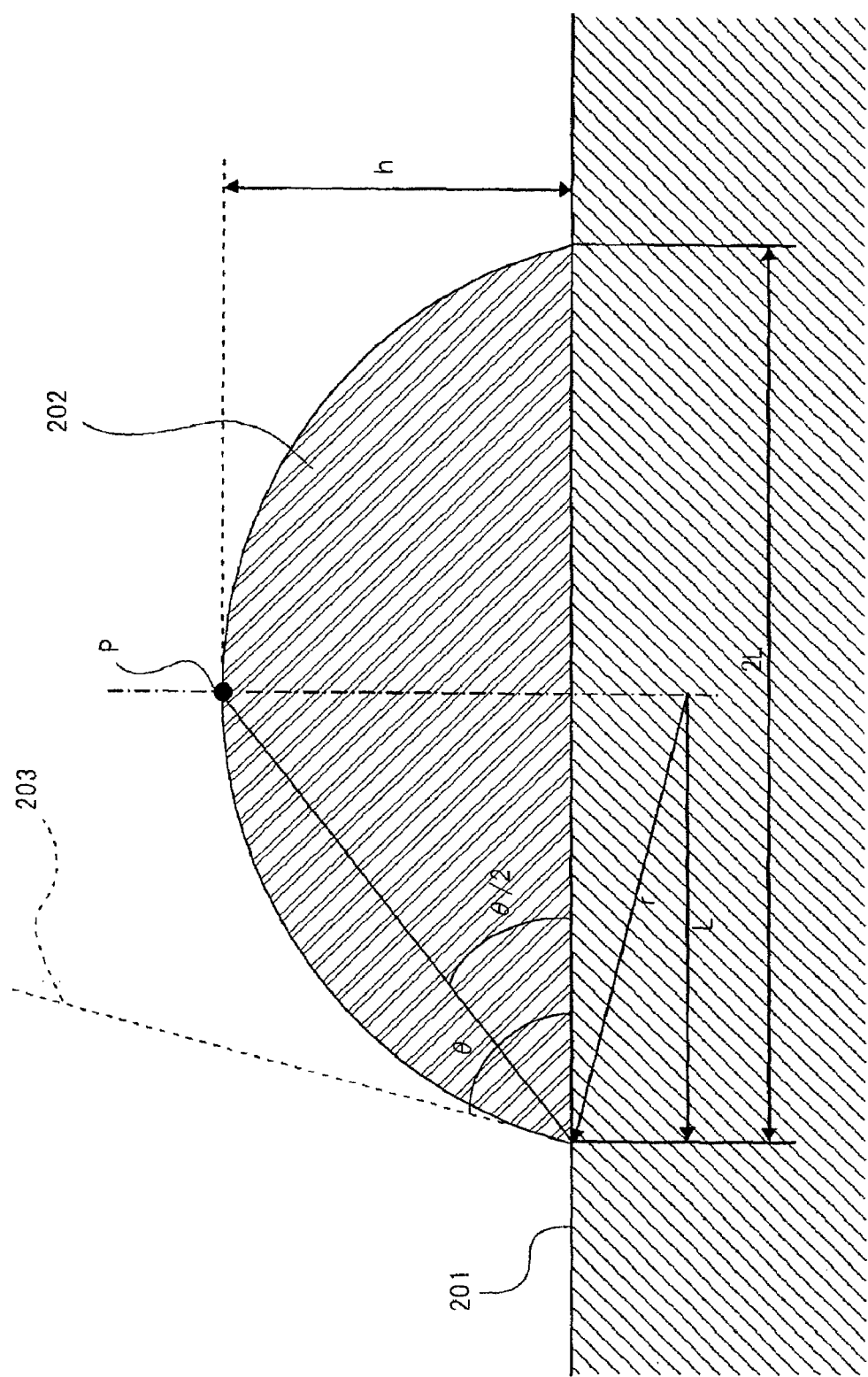
FIG. 13 is a sectional view showing droplets for explaining the relation between the height h of droplets, the angle of contact $\theta$ of droplets, and the width 2 L of droplets.

Because small volumes of liquid are handled in the electrophoresis chip of the present embodiment, the influence of gravity is nearly negligible. In this case, as shown in FIG. 13, the height h of droplet 202 from the apex P of droplet 202 to the bottom surface 201 of channel can be calculated by:

$$h = L \cdot \tan(\theta/2)$$

as shown in FIG. 12, where θ is the angle of contact of droplet 202 at the border between the surface of droplet 202 and air, and the angle is formed by the surface of the edge of droplet 202 (strictly speaking, tangent 203 of the surface) and bottom surface 201 of the channel, and 2 L is the width of droplet 202 that is parallel to bottom surface 201 of the channel. If the section of a droplet is considered, that is perpendicular to the bottom surface of the channel and that passes through the apex of the droplet in a state in which droplets are formed, to the maximum size at which adjacent droplets do not merge with each other, the surface of the droplet can be approximated by joining the bottom surface of the channel and the apex of the droplet by a substantially circular arc.

Accordingly, when a small amount of solution is introduced into channel 304 in the present embodiment, droplet 401 is formed in channel 304 as shown in FIG. 11B. Explanation here regards the state in which this droplet 401 reaches the size limit that immediately precedes contact with an adjacent droplet in a direction parallel to the section taken along line A-A', i.e., the state in which droplets are formed to the maximum size wherein adjacent droplets do not merge. In this state, compared to droplet 202 shown in FIG. 13, the following equation is realized:

$$h_A = L_A \cdot \tan(\theta_A/2)$$

where the droplet height from the apex of droplet 401 to the bottom surface of the channel is $h_A$, the width of droplet 401 in a direction parallel to the bottom surface of the channel is $2 L_A$, and the angle, formed by the surface of the edge of droplet 401 and the bottom surface of the channel, is the angle of contact $\theta_A$ of droplet 401. Here, the bottom surface of the channel refers to the surface of water-repellant film 303 formed on chip substrate 301.

However, when the height $h_A$ of this droplet is greater than the height H of the side-walls of the channel, the droplet will overflow the upper surface of the channel before contacting and merging with adjacent droplets. Accordingly, the condition $H > h_A$ must be satisfied in order to form a channel that is filled with solution in which adjacent droplets contact and merge with each other at least in a direction parallel to the section A-A' to enable electrophoresis without the overflow of solution from the upper surface of the channel. In other words, the side-walls of the channel must satisfy the relation: $H > L_A \cdot \tan(\theta_A/2)$. In addition, a prescribed height H of the channel side-walls correlates with the configuration of the pattern that is formed on the bottom surface of the channel and can be set according to the configuration of the pattern.

Similarly, in order for solution to uniformly fill the channel in a direction parallel to section B-B' of the channel, if the height of the droplet is $h_B$, the width of the droplet is $2 L_B$, and the angle of contact of the droplet is $\theta_B$ in the enlarged sectional view shown in FIG. 12, the equation $h_B = L_B \cdot \tan(\theta_B/2)$ will be realized and the condition $H > h_B$ must therefore be satisfied. In other words, the side-walls of the channel must satisfy the relation $H > L_B \cdot \tan(\theta_B/2)$.

Normally, when water-repellant film 303 is formed by a film coating that lacks anisotropy, the angle of contact of a droplet is $\theta_A=\theta_B$. However, when micropillars are used that allow production of an anisotropic arrangement, the angles of contact $\theta_A$ and $\theta_B$ do not necessarily match. In addition, the angle of contact $\theta$ will not exceed 110° in a water-repellant film that is normally obtained. Since $\tan(110/2)\approx 1.43<1.5$, the sidewalls of the channel will generally be sufficient if the relation H>1.5·L is satisfied.

According to the present embodiment as described hereinabove, a pattern is formed on the bottom surface of the channel to form a channel that has side-walls of a prescribed height H or more that is determined according to the pattern. In other words, in the electrophoresis chip of the present embodiment, in contrast with the first embodiment in which the upper surface of the channel is sealed by a cover, the channel is open to an environment in which gas is present, whereby the required condition is that the channel have side-walls of a prescribed height of at least H.

According to this configuration, a channel can be realized that acts as a flow path under specific conditions and that under specific conditions acts as wells that can each hold droplets in isolation in the channel. Thus, according to the electrophoresis chip of the present embodiment, an improved process that until now was not possible to achieve can be realized for using a PMF method to identify proteins that have been separated and detected.

Explanation next regards an example of the method of using this electrophoresis chip.

Channel 304 is filled with a sample solution that contains ampholyte and in which proteins and peptides are mixed as the sample that is to be separated. In addition, reservoirs 305 and 306 are filled with acidic and alkaline liquids for use as electrodes, and voltage is applied to the acidic side as the cathode and the alkaline side as the anode. Bottlenecks 311 and 312 serve the purpose of preventing excessive unintended mixing of the electrode liquids and sample liquid. The application of voltage forms a hydrogen ion concentration gradient in the channel. The proteins and peptides that are spread within channel 304 then, according to the channel length or applied voltage value, shift and, over the course of several minutes, collect at channel positions at which the hydrogen ion concentrations match the isoelectric points characteristic of these proteins and peptides. After each of the proteins and peptides have been collected and separated at specific positions in channel 304 according to the isoelectric points of each, the electrophoresis chip is, for example, subjected to quick cooling to fix this separated state and the sample liquid is frozen and fixed in the channel while maintaining the separated state.

The separated sample liquid can then be freeze-dried by vacuum-evacuating the surroundings of the electrophoresis chip. In this state, cover 302 that is made of rubber may be detached, or cover 302 may be left attached as is, but matrix solution is dripped only into wells of one well row of two wells rows. In this case, the amount of drip is made sufficiently small such that the droplets that are formed in the wells do not contact adjacent droplets. In this way, a matrix solution can be added to proteins that have been separated while maintaining the separated state at the resolving power of the well size. In addition, if the amount of matrix solution is insufficient, the addition of a solution may be repeated over a plurality of times such as by once drying the wells and then adding the matrix solution again. Alternatively, if a matrix solution and proteins that have been freeze-dried are not satisfactorily mixed, a substance that is difficult to dry may be used as the solvent of the matrix solution to guarantee a long mixing time before drying, or the solvent vapor pressure surrounding the chip may be raised to delay the drying speed of the solvent and thus guarantee a long mixing time.

After drying the matrix solution, chip substrate 301 is installed in a matrix-assisted laser desorption/ionization mass spectrometer (MALDI-MS) with cover 302 detached. Then, the proteins and peptides are detected by laser scanning for each well of a one well row of the two rows of wells that make up the plurality of wells that are arranged along the channel as shown in FIG. 11A, whereby information of the molecular weight of proteins and peptides before digestion can first be obtained. An internal standard can be mixed into the sample liquid and information of the isoelectric points of the sample can obtained based on the isoelectric point of the internal standard.

Channel 304 joins reservoirs 305 and 306 in a single straight line and the proteins and peptides collected in the wells of a one well row are therefore similarly collected in the wells of the other well row. By taking advantage of this property, the digest of proteins and peptides that have been detected in a one well row of two well rows is formed in the other well row, and mass spectrometry enables the identification of the detected proteins and peptides.

In other words, a trypsin solution is added to the wells of the other well row and the proteins and peptides in the wells are digested. The digestion takes at least five minutes, and the surroundings of the electrophoresis chip are therefore maintained at high solvent humidity by increasing the humidity of the vapor of the main volatile component of the solvent to suppress drying of the small amount of solution. At this time, beads in which trypsin is linked are used to enable the elimination of autolysis, allow an increase in efficiency, and enable suppression of contamination due to trypsin digests.

Although trypsin is offered here as a digestive enzyme, other digestive enzymes may also be used. In addition, although a configuration having two well rows was described in the present embodiment, the configuration is not limited to two rows. Increasing the number of well rows to three rows or four rows to carry out mass spectrometry by processing that uses various types of digestive enzymes can increase the amount of information and can raise the rate of identification.

A matrix solution is next added to the digest by the method described above to carry out mass spectrometry. As with the PMF method, proteins and peptides before digestion can be identified by searching the mass data of these digests in a database. At this time, adding the already known information of isoelectric points and information of the molecular weight of the proteins and peptides before digestion enables an improvement of the identification rate.

Although an identification method similar to the PMF method was described in the present embodiment, methods such as Edman degradation or C-terminal analysis can also be employed because proteins and peptides that have been separated in the channel can be handled independently without intermixing by using wells. The present invention can be applied not only to identification but also to a broad variety of applications such as the investigation of reactions to antibodies. According to the present invention, these completely differing functions that could not be realized in the related art can be incorporated in an electrophoresis chip.

The present embodiment as described hereinabove employs a configuration in which a pattern is formed on the bottom surface of a channel by using differences in hydrophilic and hydrophobic properties, and this pattern is formed such that a hydrophilic area is surrounded by hydrophobic areas and the side-walls of the channel. By means of this configuration, a channel can be realized that functions as a flow path under conditions of an ample amount of liquid and that functions as wells that can hold droplets independently in the channel under conditions in which there is a limited amount of liquid.

Accordingly, the electrophoresis chip of the present embodiment can realize improved processing that could not previously be realized, such as the above-described identification by a PMF method of proteins that have been separated and detected. As the pattern on the bottom surface of the channel, a pattern was used in the present embodiment similar to the pattern shown in FIG. 6 in which a hydrophilic area is surrounded by hydrophobic areas and the side-walls of the channel, but as stated in the first embodiment, the present invention is not limited to this type of pattern. Although water-repellant film 303 was used as the hydrophobic area in the present embodiment, another thin film such as a film coating that makes up an area having a lower hydrophilic property than the hydrophilic areas formed by the surface of chip substrate 301 may also be used. In this construction, the same effects as previously described can be obtained even though the angle of contact θ of droplets is lower.

In addition, as in the first embodiment, in the present embodiment, micro-pillars that make up an array construction composed of a plurality of protrusions that are sufficiently smaller than droplets can be formed on the bottom surface of the channel, whereby the hydrophilic property can be freely controlled by varying the density of these protrusions to change the multiplication factor of the surface area of the bottom surface. The array construction that is composed of a plurality of protrusions can of course also employ the patterns shown in FIGS. 8 to 10, and can obtain the same effects as previously described.

Although the invention of the present application has been described with reference to embodiments, the invention of the present application is not limited to the above-described embodiments. The configuration and details of the invention of the present application are open to various modifications within the scope of the invention of the present application that would be obvious to those skilled in the art.

This application claims priority based on Japanese Patent Application 2007-340363 which was submitted on Dec. 28, 2007 and includes all of the disclosures of that application.

What is claimed is:

1. An electrophoresis chip, said electrophoresis chip being provided with a channel that is filled with a solution in which a sample is dissolved, and said electrophoresis chip being configured to implement electrophoresis by applying voltage along said channel in a state in which said channel is hermetically sealed to separate said sample in said channel, and after said electrophoresis is performed, to carry out mass spectrometry of said sample by scanning a laser along said channel in a state in which said channel is open to an environment in which gas is present; wherein
   a pattern for holding said solution as droplets being formed on the bottom surface of said channel; and
   said pattern being made into a pattern in which a first hydrophilic area is surrounded by at least a second hydrophilic area in which the hydrophilic property is lower than that of said first hydrophilic area.

2. The electrophoresis chip according to claim 1, wherein said pattern is a pattern in which said first hydrophilic area is surrounded by said second hydrophilic area and side-walls of said channel.

3. An electrophoresis chip, said electrophoresis chip being provided with a channel that is filled with a solution in which a sample is dissolved, and said electrophoresis chip being configured to implement electrophoresis by applying voltage along said channel in a state in which said channel is hermetically sealed to separate said sample in said channel, and after said electrophoresis is performed, to carry out mass spectrometry of said sample by scanning a laser along said channel in a state in which said channel is open to an environment in which gas is present; wherein:
   a pattern for holding said solution as droplets being formed on the bottom surface of said channel; and
   said pattern being made into a pattern in which a hydrophilic area is surrounded by at least a hydrophobic area.

4. The electrophoresis chip according to claim 3, wherein said pattern is a pattern in which said hydrophilic area is surrounded by said hydrophobic area and side-walls of said channel.

5. An electrophoresis chip provided with: a groove-shaped channel that is filled with a solution in which a sample is dissolved, a substrate that forms the bottom surface of said channel, and a frame member that forms side-walls of said channel and that can be detached from said substrate; said electrophoresis chip being configured to implement electrophoresis by applying voltage along said channel in a state in which said solution in said channel is open to an environment in which gas is present to separate said sample in said channel, and after said electrophoresis, to implement mass spectrometry of said sample by scanning a laser along said channel in a state in which said frame member has been removed from said substrate; wherein:
   a pattern for holding said solution as droplets is formed on said bottom surface of said channel;
   said pattern is a pattern in which a first hydrophilic area is surrounded by at least a second hydrophilic area in which the hydrophilic property is less than that of said first hydrophilic area; and
   the height from said bottom surface of said side-walls of said channel is formed to at least a prescribed height that correlates with said pattern.

6. The electrophoresis chip according to claim 5, wherein said pattern is a pattern in which said first hydrophilic area is surrounded by said side-walls of said channel and said second hydrophilic area.

7. The electrophoresis chip according to claim 5, wherein:

$$H > L \cdot \tan(\theta/2)$$

where said prescribed height of said side-walls of said channel is H, and
   when in a state in which said droplets are formed to maximum size such that droplets held in said pattern to not contact with adjacent said droplets, the width of said droplets in a direction parallel to said bottom surface of said channel is 2 L, and the angle of contact of said droplets, that is formed by the surface of the edge of said droplets and said bottom surface of said channel, is θ.

8. The electrophoresis chip according to claim 5, wherein the difference in said hydrophilic properties in said pattern is formed by the difference in densities produced by a plurality of protrusions formed on said bottom surface of said channel.

9. An electrophoresis chip, said electrophoresis chip being provided with a groove-shaped channel that is filled with a solution in which a sample is dissolved, a substrate that forms the bottom surface of said channel, and a frame member that forms side-walls of said channel and that can be detached from said substrate; and said electrophoresis chip being configured to implement electrophoresis by applying voltage along said channel in a state in which said solution in said channel is open to an environment in which gas is present to separate said sample in said channel, and after said electrophoresis is performed, to implement mass spectrometry of said sample by scanning a laser along said channel in a state in which said frame member has been removed from said substrate; wherein:

a pattern for holding said solution as droplets is formed on said bottom surface of said channel;

said pattern is a pattern in which a hydrophilic area is surrounded by at least a hydrophobic area; and the height from said bottom surface of said side-walls of said channel is formed to at least a prescribed height that correlates with said pattern.

10. The electrophoresis chip according to claim 9, wherein said pattern is a pattern in which said hydrophilic area is surrounded by said side-walls of said channel and said hydrophobic area.

* * * * *